United States Patent [19]

Dory

[11] Patent Number: 5,158,070
[45] Date of Patent: Oct. 27, 1992

[54] METHOD FOR THE LOCALIZED DESTRUCTION OF SOFT STRUCTURES USING NEGATIVE PRESSURE ELASTIC WAVES

[75] Inventor: Jacques Dory, Coupvray, France

[73] Assignee: EDAP International, S.A., France

[21] Appl. No.: 554,118

[22] Filed: Jul. 18, 1990

Related U.S. Application Data

[60] Continuation-in-part of Ser. No. 368,906, Jun. 19, 1989, which is a continuation of Ser. No. 37,369, Apr. 13, 1987, abandoned, which is a division of Ser. No. 728,905, Apr. 30, 1985, now Re. 33,590, which is a continuation-in-part of Ser. No. 674,889, Nov. 26, 1984, Pat. No. 4,617,931.

[30] Foreign Application Priority Data

Oct. 6, 1988 [FR] France .................................. 88 13094

[51] Int. Cl.$^5$ ............................................. A61B 17/00
[52] U.S. Cl. ........................... 128/240 AA; 128/660.03
[58] Field of Search ...................... 128/24 AA, 660.03

[56] References Cited

U.S. PATENT DOCUMENTS

| | | | |
|---|---|---|---|
| 4,315,514 | 2/1982 | Drewes et al. | 128/24 A |
| 4,617,931 | 10/1986 | Dory | 128/24 A |
| 4,620,546 | 11/1986 | Aida et al. | 128/24 A |
| 4,858,597 | 8/1989 | Kurtze et al. | 128/24 A |

*Primary Examiner*—Lee S. Cohen
*Assistant Examiner*—Krista M. Pfaffle
*Attorney, Agent, or Firm*—William A. Drucker

[57] ABSTRACT

The method for the localized destruction of soft structures using negative pressure elastic waves, comprises the steps of generating at a predetermined rate comprised between a few Hz and 3 KHz, trains of elastic pressure waves, said waves having a frequency between 0.3 and 10 MHz, each of said trains having a duration between 1 microsecond and 1 millisecond and comprising negative going oscillations; focussing said waves into a beam; transmitting and directing said beam onto the target through a liquid coupling medium and adjusting the power of said elastic pressure wave at a predetermined value.

3 Claims, No Drawings

METHOD FOR THE LOCALIZED DESTRUCTION OF SOFT STRUCTURES USING NEGATIVE PRESSURE ELASTIC WAVES

RELATED APPLICATIONS

This is a continuation-in-part of copending application Ser. No. 368,906 filed Jun. 19, 1989, which is a continuation of Ser. No. 037,369 filed Apr. 13, 1987, abandoned, which is a division of Ser. No. 728,905 filed Apr. 30, 1985, U.S. Pat. No. 4,658,828, reissued on May 21, 1991 as U.S. Pat. No. RE. 33,590, which is a continuation-in-part of Ser. No. 674,889 filed Nov. 26, 1984, issued as U.S. Pat. No. 4,617,931 on Oct. 21, 1986, Reexamination Certificate B1-4,617,931 of Jul. 12, 1988. Priority is claimed from French application 83.20041 of Dec. 14, 1983 under 35 USC 119.

BACKGROUND OF THE INVENTION

1. Field of the Invention

The invention relates to a method for destroying a target formed by soft structures localized within a medium which prevents having access thereto directly by mechanical means.

Among the applications of such a method may be mentioned the destruction of living cells, e.g. tumoral cells inside the body of a patient, or the coloring of a material through its mass by causing microballs to explode and release dyes, or the localized use of a chemical reaction, by releasing material capable of reacting and contained in microballs.

The destruction by extracorporeal means of a target formed by mechanically resilient structures takes place at the present time using positive pressure elastic waves which subject said structures to compression forces.

By way of example, in known lithotriptors, elastic pulses of a duration of about a microsecond, focussed on a calculus pulverize the latter.

More particularly, in lithotriptors with an emitting source distributed over a surface and of piezoelectric type, these elastic waves, unless very specific arrangements are made, comprise positive pressure half waves (with respect to the mean pressure of the oscillation) and negative half waves. However, it is known that the latter do not contribute to the destruction of the calculi and have on the contrary the harmful effect of causing the formation of a barrier formed of bubbles generated by cavitation and which hinders the propagation of the beam, even interrupting it.

2. Description of the Prior Art

The prior art relative to the destruction of soft targets is formed, for example, by hyperthermia, i.e. localized heating at well defined temperatures. For this, trains of elastic waves are used focussed on the target. These wave trains may be generated (as in lithotripsy) by an emitting source distributed over a surface and of piezoelectric type but, whereas in lithotripsy pulses are generally used of very short duration (of about 1 $\mu s$) and considerable peak powers (of the order of several tens of kilowatts), in hyperthermia the powers are reduced to peak values of 10 to 100 watts, for example, and the wave trains are emitted over much longer periods (reaching a second for example) sufficient to cause heating. In the case of hyperthermia, the frequencies are of the order of 0.5 to 5 MHz.

SUMMARY OF THE INVENTION

The invention starts from the discovery of the fact that soft structures can be efficiently destroyed using negative pressure waves of short duration, by tractive forces which tear them.

The method for the localized destruction of soft structures according to the invention comprises the step of:

i) generating, at a predetermined rate comprised between a few Hz and 3 KHz, trains of elastic pressure waves, said waves having a frequency between 3.0 and 10 MHz, each of said trains having a duration between 1 microsecond and 1 millisecond and comprising negative going oscillations;
ii) focussing said waves into a beam;
iv) adjusting the power of said elastic pressure waves at a predetermined value.

In a preferred embodiment, said oscillations comprise positive and negative peaks, the negative peak having an amplitude substantially larger than that of the positive peaks.

According to an advantageous feature, the step iv) comprises:

iv-a) adjusting said power at a first value substantially lower than said predetermined value,
iv-b) receiving the energy of the elastic pressure waves reflected from the target and displaying echoes from the reflected energy,
iv-c) increasing the power until a threshold is reached for which the displayed echoes disappear and
iv-d) adjusting the power short of said threshold.

The disappearance of the echoes corresponds in fact to the appearance of the cavitation phenomenon in the region of the focal point and the power thus adjusted will then be more efficient for destroying tumoral cells.

DESCRIPTION OF THE PREFERRED EMBODIMENT

Other features and advantages of the invention will be clear from the following description given by way of example.

EXAMPLE

A lithotriptor is used of piezoelectric type with an emission source distributed over a surface, advantageously of the kind described in the patent FR 83 20041 filed on Dec. 14th, 1992.

To obtain a preponderance of negative ultrasonic waves, it is sufficient for example to change the direction of the windings of the transformer which couples the power ceramic transducer to the pulse generator, so as to energize said transducer with pulse trains in which the negative half waves are preponderant.

It will be noted that a lithotriptor of electrohydraulic type, i.e. with spark path in a coupling liquid, is not capable of generating negative pulses and would therefore not be usable.

The waveform, such as defined by that of the electric signal energizing the transducer, consists of frequency oscillations advantageously between 300 KHz and 1 MHz for destroying deep tissues and between 5 and 10 MHz for destroying surface tissues. The wave trains or "shots" have for example durations between 1 $\mu s$ and 1 ms and the firing rate is for example between a few Hz and 2 or 3 KHz, these values not being limitative. The lowest firing rates are those which give the best echographic image of the target. The wave train durations are advantageously determined so that destruction of the cells takes place mainly by mechanical stress : longer durations would cause the appearance of a hyperthermia phenomenon.

The method comprises a phase for the prior adjustment of the emission power of the main transducer, during which the peak power of the oscillations is first of all adjusted to a low value (a few watts for example) while the wave train duration is itself adjusted to its minimum value and their rate to its maximum value. The echoes coming from reflection from the target of the negative pulses emitted by the power transducer are picked up by the auxiliary echography transducer of the lithotriptor, making it possible to display the distribution of energy in the focal spot, in accordance with the method described in the above-mentioned patent. Then, the emission power is progressively increased until the echoes, from the target disappear: there then generally appears, on the display screen a small bright cloud which indicates the appearance of the cavitation phenomenon at the focal point.

If the power is further increased, cavitation would develop between the emission surface and the focal point, which would no longer be irradiated.

The final power is adjusted a little short of the threshold at which the echoes situated in the focal zone disappear and then the wave train duration and rate are appropriately adjusted.

By way of example, the peak power selected will be of the order of a few kilowatts, corresponding to peak pressures of about 50 to 60 bars.

The negative oscillations used act mainly by mechanical stress, by exerting tractive forces which tear the cells (whereas soft structures withstand much better the compression effects generated by positive oscillations).

The wave train power, duration and rates can be adjusted and the appropriate polarity of the oscillations energizing the transducer can be obtained by a man skilled in the art and may be carried out in different ways without departing from the scope and spirit of the invention.

By way of example, the appearance of cavitation in the focal region could be detected using type A echography and by observing the deformation of the echoes as a function of the emission power.

What is claimed is:

1. A method for the localized destruction of a target having a soft structure, comprising the steps of:
    i) generating, at a predetermined rate, trains of elastic pressure waves, said waves having a frequency between 3.0 and 10 MHz, each of said trains having a duration between 1 microsecond and 1 millisecond and comprising negative going oscillations;
    ii) focussing said waves into a beam;
    iii) transmitting and directing said beam onto the target and
    iv) adjusting the power of said trains of elastic pressure waves to a particular value which allows reflected energy from said target to be displayed as echoes.

2. The method as claimed in claim 1, wherein said oscillations comprise positive and negative peaks, the negative peaks having an amplitude substantially larger than that of the positive peaks.

3. The method as claimed in claim 1, wherein step iv) comprises:
    iv-a) adjusting said power at a first value substantially lower than said particular value;
    iv-b) receiving the energy of the elastic pressure waves reflected from the target and displaying echoes from the reflected energy;
    iv-c) increasing the power until a threshold is reached for which the displayed echoes disappear and
    iv-d) adjusting the power short of said threshold.

* * * * *

UNITED STATES PATENT AND TRADEMARK OFFICE
CERTIFICATE OF CORRECTION

PATENT NO. : 5,158,070
DATED : October 27, 1992
INVENTOR(S) : Jacques Dory

It is certified that error appears in the above-identified patent and that said Letters Patent is hereby corrected as shown below:

On the title page, item [60]:

(60) Continuation of Ser. No. 418,304, Oct. 6, 1989, abandoned, which is a continuation-in-part of Ser. No. 368,906, Jun. 19, 1989, which is a continuation of Ser. No. 37,369, Apr. 13, 1987, abandoned, which is a division of Ser. No. 728,905, Apr. 30, 1985, now RE 33,590, which is a continuation-in-part of Ser. No. 674,889, Nov. 26, 1984, Pat. No. 4,617,931.

Signed and Sealed this

Twenty-fourth Day of January, 1995

Attest:

BRUCE LEHMAN

Attesting Officer

Commissioner of Patents and Trademarks